United States Patent [19]
Niiyama et al.

[11] Patent Number: 5,266,269
[45] Date of Patent: Nov. 30, 1993

[54] HEMATOLOGY ANALYZER

[75] Inventors: Yoshihiro Niiyama; Katsumi Yoshikawa, both of Tokyo, Japan

[73] Assignee: Nihon Kohden Corporation, Tokyo, Japan

[21] Appl. No.: 859,030

[22] Filed: Mar. 27, 1992

[30] Foreign Application Priority Data

Mar. 31, 1991 [JP] Japan .................................. 3-93121

[51] Int. Cl.[5] .............................................. G01N 33/00
[52] U.S. Cl. ............................................ 422/73; 422/63;
422/64; 73/864.81
[58] Field of Search ........................... 422/63, 64, 73;
73/64.56, 61.41, 864.11, 864.81, 864.21;
220/23.86, 23.83, 478, 479, 400

[56] References Cited

U.S. PATENT DOCUMENTS

| | | | |
|---|---|---|---|
| 4,244,919 | 1/1981 | Chen | 422/63 |
| 4,441,374 | 4/1984 | Suzuki | 73/864.21 |
| 4,631,483 | 12/1986 | Proni et al. | 73/864.11 |
| 4,699,766 | 10/1987 | Yamashita | 422/64 |
| 4,729,876 | 3/1988 | Hennessy et al. | 422/63 |

*Primary Examiner*—James C. Housel
*Assistant Examiner*—Lien Tran
*Attorney, Agent, or Firm*—Sughrue, Mion, Zinn, Macpeak & Seas

[57] ABSTRACT

A hematology analyzer includes a first measuring container having a first sensing device, a second measuring container having a second sensing device, a first auxiliary container diluting blood collected by a sampling nozzle and being arranged so as to allow the first diluted blood solution to flow into the first measuring container; a second auxiliary container further diluting the first diluted blood solution collected in the first auxiliary container by the sampling nozzle and being arranged so as to allow the second diluted blood solution to flow into the second measuring container, and first blood cells contained in the first diluted blood solution poured into the first measuring container from the first auxiliary container are measured by the first sensing device, and second blood cells contained in the second diluted blood solution poured into the second measuring container from the second auxiliary container are measured by the second sensing device.

7 Claims, 10 Drawing Sheets

HEMATOLOGY ANALYZER

BACKGROUND OF THE INVENTION

The invention relates to a hematology analyzer for counting and measuring the number of blood cells such as white blood cells and red blood cells in a blood sample or the like.

A method of counting and measuring white blood cells and red blood cells in blood with a hematology analyzer generally involves the use of an electric resistance detection system and the processes of measuring white blood cells while diluting the blood by 1/200 and of measuring red blood cells while diluting the blood further by 1/200 to prepare a 1/40000 diluted blood solution.

Figure 14:
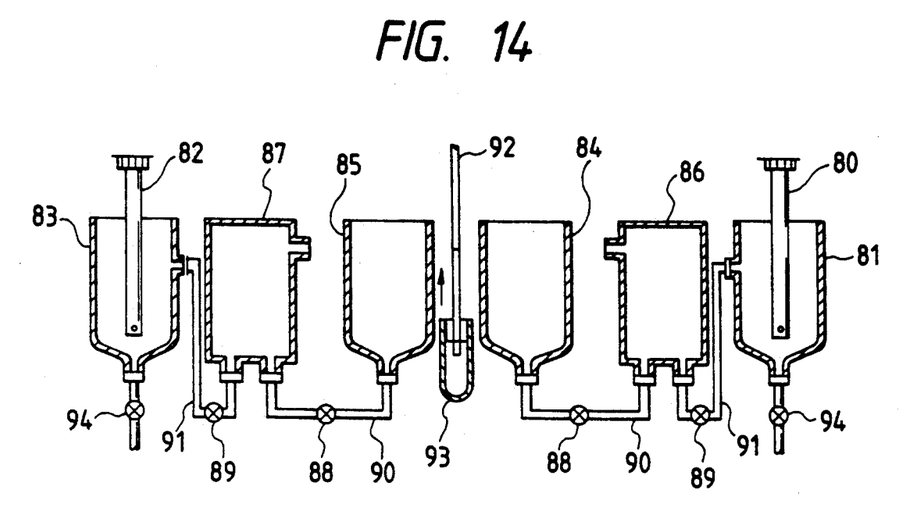
FIG. 14 is a diagram showing a configuration of a conventional hematology analyzer.

FIG. 14 shows a configuration of a conventional hematology analyzer. An aperture tube 80, which is disposed in a measuring cup 81, measures white blood cells, while an aperture tube 82, which is disposed in a measuring cup 83, measures red blood cells and the like. Between diluting cups 84, 85 and the measuring cups 81, 83 are auxiliary chambers 86, 87 for supplying solutions, with tubes 90, 91, each having a solenoid valve along its tube path, coupling between the diluting cups 84, 85 and the auxiliary chambers 86, 87, and between the auxiliary chambers 86, 87 and the measuring cups 81, 83, respectively. This hematology analyzer further includes a sampling nozzle 92 that absorbs not only patient's whole blood which will serve as a sample, but also diluted blood.

Figure 15:
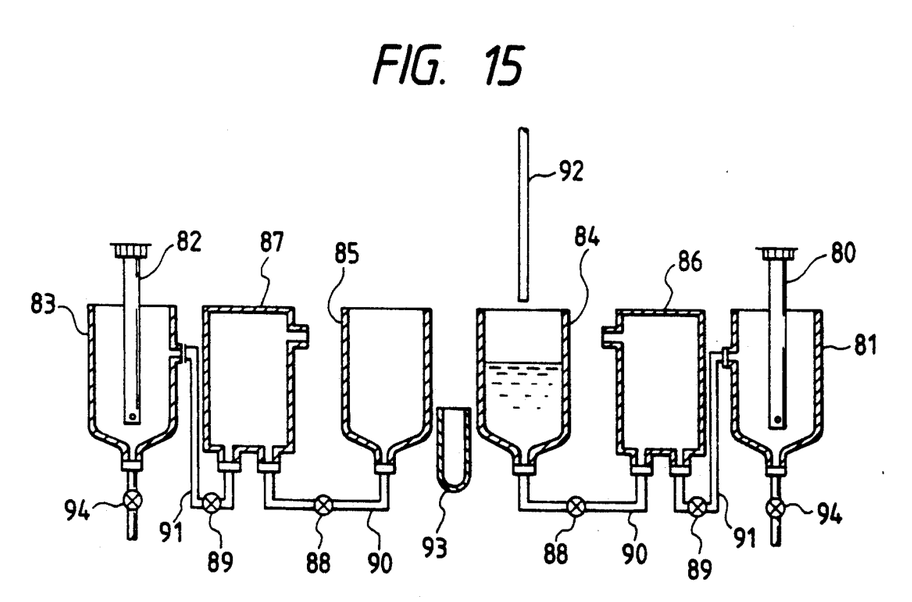
FIG. 15 is a diagram illustrative of an operation of the conventional hematology analyzer.

As shown in FIG. 15, to count and measure blood cells with such a hematology analyzer, a predetermined amount of blood is first collected from a sampling cup 93 by the sampling nozzle 92, then discharged into the diluting cup 84 (on the right) and diluted by 1/200 while simultaneously pouring a diluting solution from the sampling nozzle 92.

Figure 16:
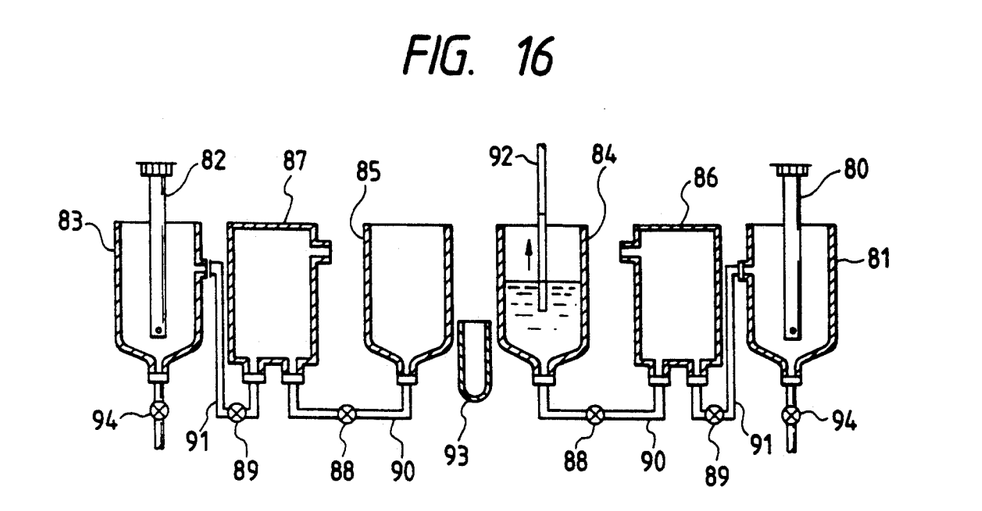
FIG. 16 is a diagram illustrative of an operation of the conventional hematology analyzer.
Figure 17:
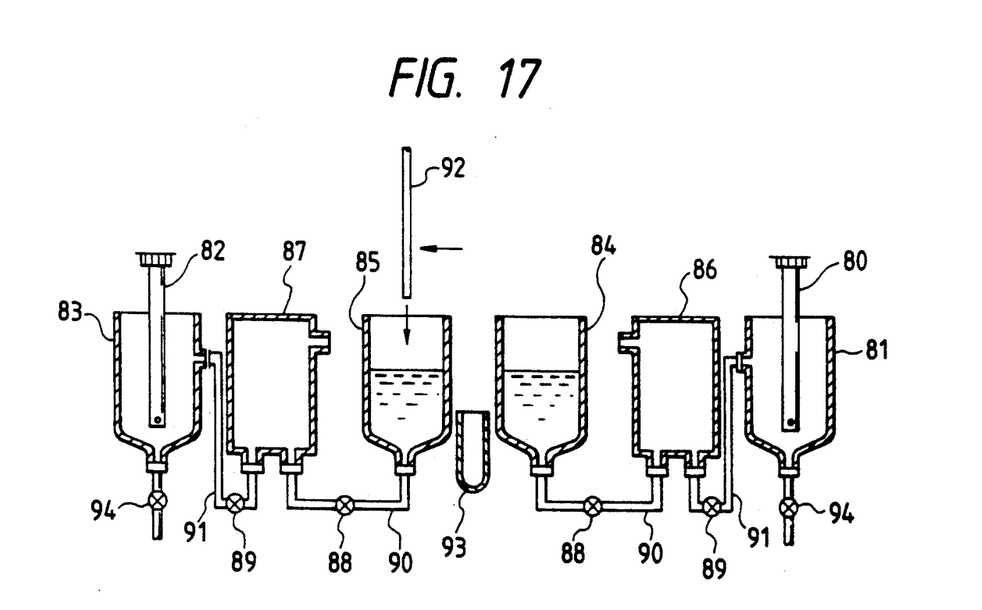
FIG. 17 is a diagram illustrative of the operation of the conventional hematology analyzer.

Thereafter, as shown in FIGS. 16, 17, the 1/200 diluted blood is drawn from the diluting cup 84 by the sampling nozzle 92, discharged into the diluting cup 85 (on the left), and diluted to 1/40000 with a diluting solution introduced from the sampling nozzle 92.

Figure 18:
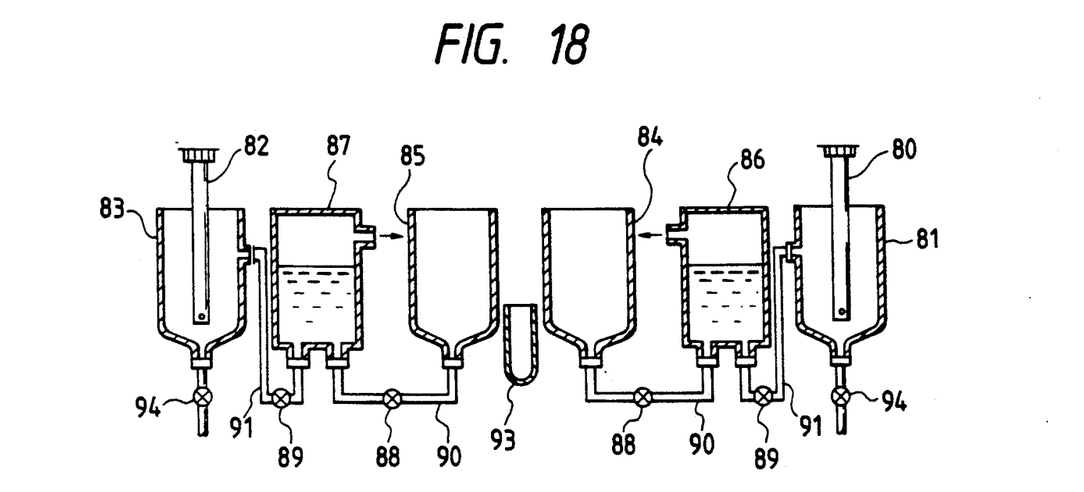
FIG. 18 is a diagram illustrative of the operation of the conventional hematology analyzer.
Figure 19:
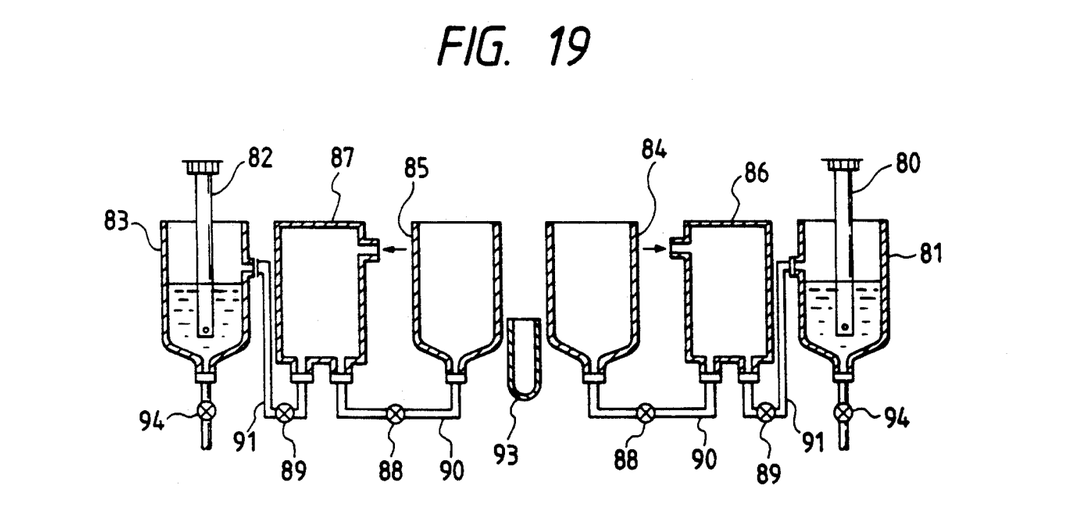
FIG. 19 is a diagram illustrative of the operation of the conventional hematology analyzer.

Successively, the auxiliary chambers 86, 87 are evacuated or emptied by a negative pressure by pumps, and the solenoid valves 88 are opened to transfer the diluted blood solutions in the diluting cups 84, 85 into the auxiliary chambers 86, 87 as shown in FIG. 18. At this point, a hemolysing reagent is injected into the auxiliary chamber 86 to destroy red blood cells. Then, the solenoid valves 88 are closed and the solenoid valves 89 are opened, and by pressuring the auxiliary chambers 86, 87 using a positive pressure, the diluted blood solutions in the auxiliary chambers 86, 87 are transferred to the measuring cups 81, 83 as shown in FIG. 19. Thereafter, the white blood cells are measured by the aperture tube 80 of the measuring cup 81, while the red blood cells and the like are measured by the aperture tube 82 of the measuring cup 83. After the measurement has been completed, the solenoid valves 94 are opened, the diluted blood solutions are discharged, and the cups 81, 83 are internally cleaned.

The above-mentioned conventional hematology analyzer requires not only the use of auxiliary chambers 86, 87 and pneumatic sources such as pumps, but also the use of tubes 90, 91 having solenoid valves 88, 89 to supply the solutions from the diluting cups 84, 85 to the measuring cups 81, 83. Such construction may occasionally cause defective supply of the solutions due to leakage from and clogging of the tubes 90, 91. The complicated structure of the system is another problem.

SUMMARY OF THE INVENTION

An object of the invention is to provide a hematology analyzer having such a simple design as to cause no defective supply of solution and no measurement error due to defective dilution by the solution remaining in the supply path.

To achieve the above object, a hematology analyzer of the invention includes: a first measuring container having a first sensing means; a second measuring container having a second sensing means; a first auxiliary container diluting blood collected by a sampling nozzle and being arranged so as to allow the first diluted blood solution to flow into the first measuring container; a second auxiliary container further diluting the first diluted blood solution collected in the first auxiliary container by the sampling nozzle and being arranged so as to allow the second diluted blood solution to flow into the second measuring container. In this hematology analyzer, first blood cells contained in the first diluted blood solution poured into the first measuring container from the first auxiliary container are measured by the first sensing means, and second blood cells contained in the second diluted blood solution poured into the second measuring container from the second auxiliary container are measured by the second sensing means.

The hematology analyzer of the invention includes that the first auxiliary container that is open on the top is rotatably arranged inside the first measuring container and the second auxiliary container that is open on the top is rotatably arranged inside the second measuring container.

The hematology analyzer of the invention further includes that flow paths for the diluted blood solutions poured from the auxiliary containers are arranged at parts of the measuring containers, respectively, and these flow paths are constricted.

According to the above-mentioned first aspect of the invention, the first diluted blood solution can be prepared in the first auxiliary container inside the first measuring container, and this first diluted blood solution can be poured into the first measuring container directly from the first auxiliary container.

Also, the second diluted blood solution can be prepared in the second auxiliary container inside the second measuring container, and this second diluted blood solution can be poured into the second measuring container directly from the second auxiliary container.

According to the above-mentioned second aspect of the invention, the first diluted blood solution in the first auxiliary container can be poured into the first measuring container directly by rotating the first auxiliary container that is open on the top.

Also, the second diluted blood solution in the second auxiliary container can be poured into the second measuring cup directly by rotating the second auxiliary container that is open on the top.

According to the above-mentioned third aspect of the invention, the diluted blood solutions respectively introduced from the first and second auxiliary containers to the first and second measuring containers can be stirred sufficiently during their passage through the constricted portions.

DETAILED DESCRIPTION OF THE PREFERRED EMBODIMENTS

Figure 1:
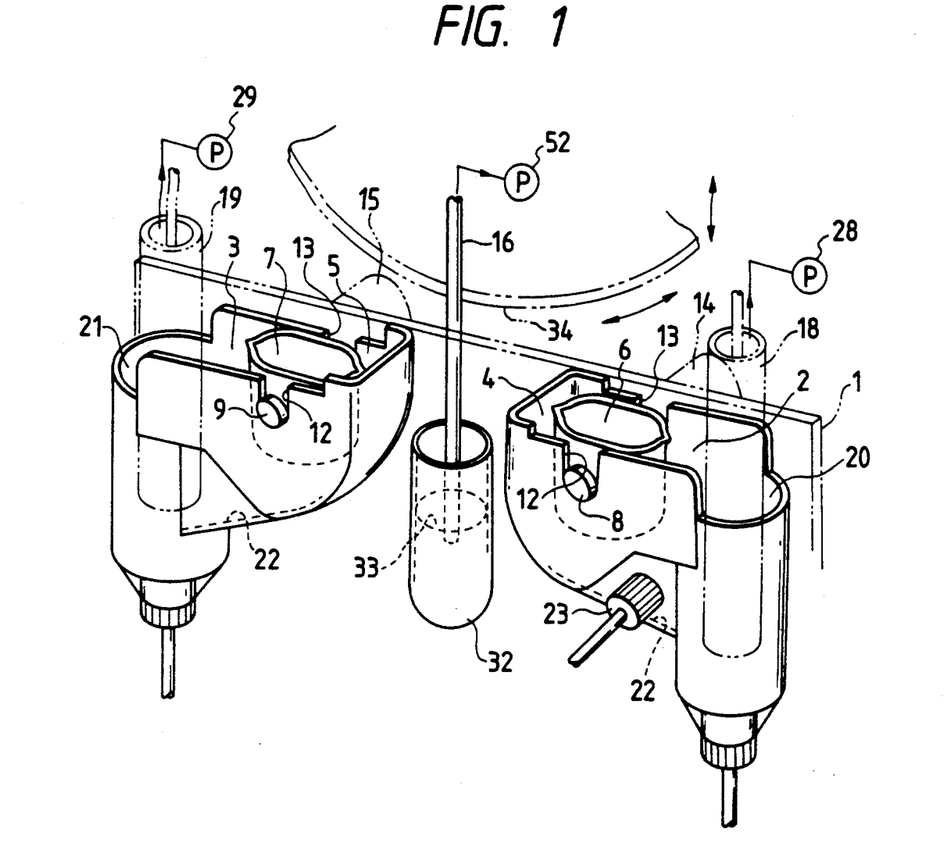
FIG. 1 is a perspective view showing a hematology analyzer which is an embodiment of the invention.

A hematology analyzer which is a specific embodiment of the invention will now be described in detail with reference to the drawings. FIG. 1 is a perspective view showing a main portion of the hematology analyzer.

Figure 2:
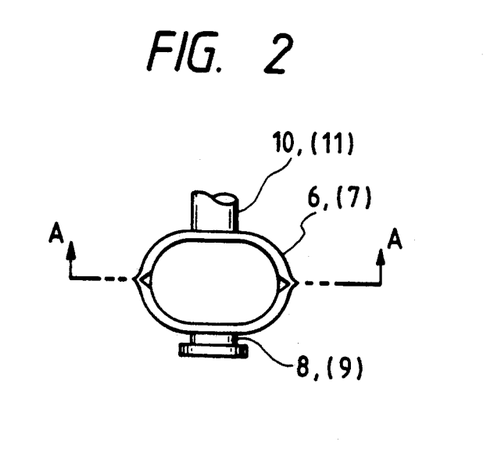
FIG. 2 is a plan view showing a sub bath of the hematology analyzer of the invention.
Figure 3:
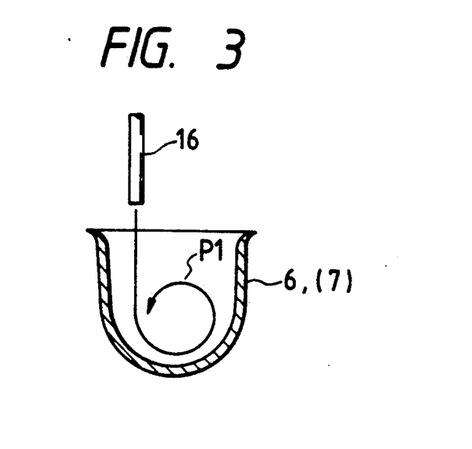
FIG. 3 is a sectional view taken along a line A—A shown in FIG. 2.

In FIG. 1, a pair of main baths 2, 3 forming first and second measuring containers are mounted on both the right and left sides and in front of a mounting plate 1. Here, the main bath 2 for white blood cells measures white blood cells, which is a first type of blood cell, while the main bath 3 for red blood cells measures red blood cells, platelets, and the like, which is a second type of blood cell. In upper portions of these main baths that are open on the top are a pair of protruding sub bath-accommodating spaces 4, 5 provided so as to confront each other on single sides thereof, and sub baths 6, 7 serving as first and second diluting auxiliary containers that are open on the top are respectively accommodated in these accommodating spaces 4, 5. These sub baths 6, 7 have their shaft portions 8, 9 and rotating shafts 10, 11 (see FIG. 2) fitted into notched recesses 12, 13, so that the sub baths 6, 7 can be rotated in both the right and left directions. The shaft portions 8, 9 serve as pivots and protrude toward the front; the rotating shafts 10, 11 protrude toward the back; and the notched recesses 12, 13 are notched both in the front and back sides of the main baths 2, 3. On the back of the mounting plate 1 are drive motors 14, 15 coupled to the rotating shafts 10, 11, so that the motors 14, 15 can rotate the sub baths 6, 7 in predetermined directions to pour the diluted blood solutions into the main baths 2, 3. As shown in FIG. 3, which is a sectional view taken along a line A—A shown in FIG. 2, each of the sub baths 6, 7 has a longitudinal section that is semicircular at the bottom, and when the blood and a diluting solution or a diluted blood solution and a diluting solution are poured into each of the sub baths 6, 7 by a sampling nozzle 16, the blood and the diluting solution or the diluted blood solution and the diluting solution are poured while forming a swirling stream such as shown by an arrow P1 in FIG. 3 and are thereby stirred and mixed well.

Figure 4:
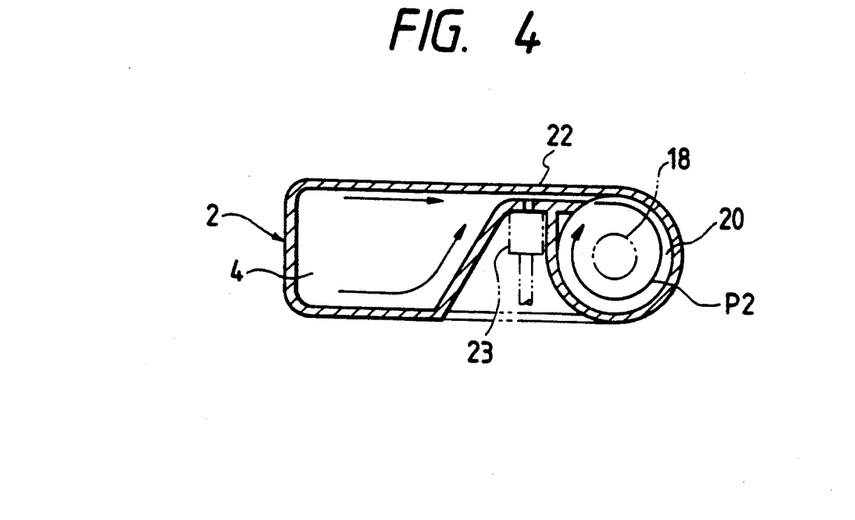
FIG. 4 is a horizontal sectional view showing a main bath of the hematology analyzer of the invention.
Figure 5:
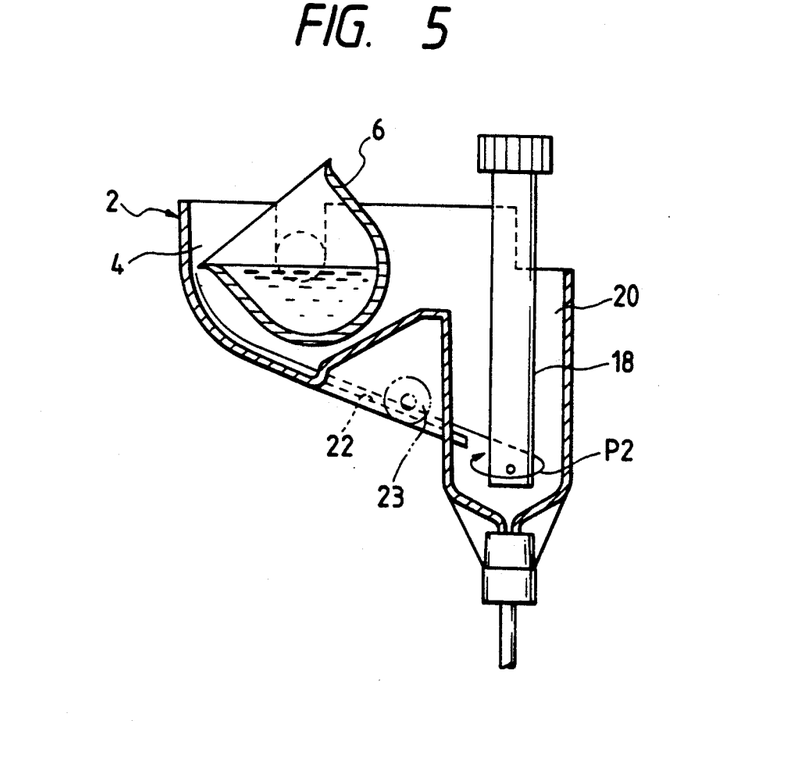
FIG. 5 is a longitudinal sectional view showing the main bath and the sub bath of the hematology analyzer of the invention.

On the other sides of the main baths 2, 3 are measuring vessels 20, 21 into which aperture tubes 18, 19 are to be inserted, each measuring vessel has a circular horizontal section. Descending paths 22 connecting between the sub bath-accommodating spaces 4, 5 and these measuring vessels 20, 21 are constricted or narrowed so as to allow the diluted blood solutions to be or splashed into the measuring vessels 20, 21. The main bath 2 for measuring white blood cells is provided with a hemolysing reagent injecting portion 23 for injecting a hemolysing reagent toward this constricted descending path 22. The hemolyzer injected from this injecting portion 23 is poured with force into the measuring vessel 20 together with the diluted blood solution supplied from the sub bath 6. At this point, since the extension of the exit of the descending path 22 coincides with the tangential direction of the section of the measuring vessel 20, the solution forms a swirling stream within the measuring vessel 20 by or splashing against the inner peripheral surface of the measuring vessel 20 as shown by an arrow P2 in FIGS. 4 and 5, and with the swirling stream successively meeting with the solution discharged from the path 22, causing the diluted blood solution and the hemolysing reagent to be stirred and mixed sufficiently. The swirling stream is similarly formed in the measuring vessel 21.

The main baths 2, 3 and the sub baths 6, 7 are symmetrically arranged in two pairs for the white blood cells and the red blood cells, ensuring excellent maintainability. In addition, if the main baths 2, 3 and the sub baths 6, 7 are made of a transparent resin, the solutions within them can visibly be checked with ease.

This hematology analyzer includes the sampling nozzle 16 that not only absorbs patient's whole blood 33 from a sampling cup 32, supplies it into the sub bath 6 together with a diluting solution, but also absorbs a 1/200 diluted blood solution within the sub bath 6 (the first diluted blood solution) and supplies it into the sub bath 7 together with a diluting solution. This sampling nozzle 16 is attached to the outer peripheral portion of a forwarding disk 34, which disk rotates and ascends and descends to transfer each sampling nozzle 16 to a predetermined position.

Figure 12:
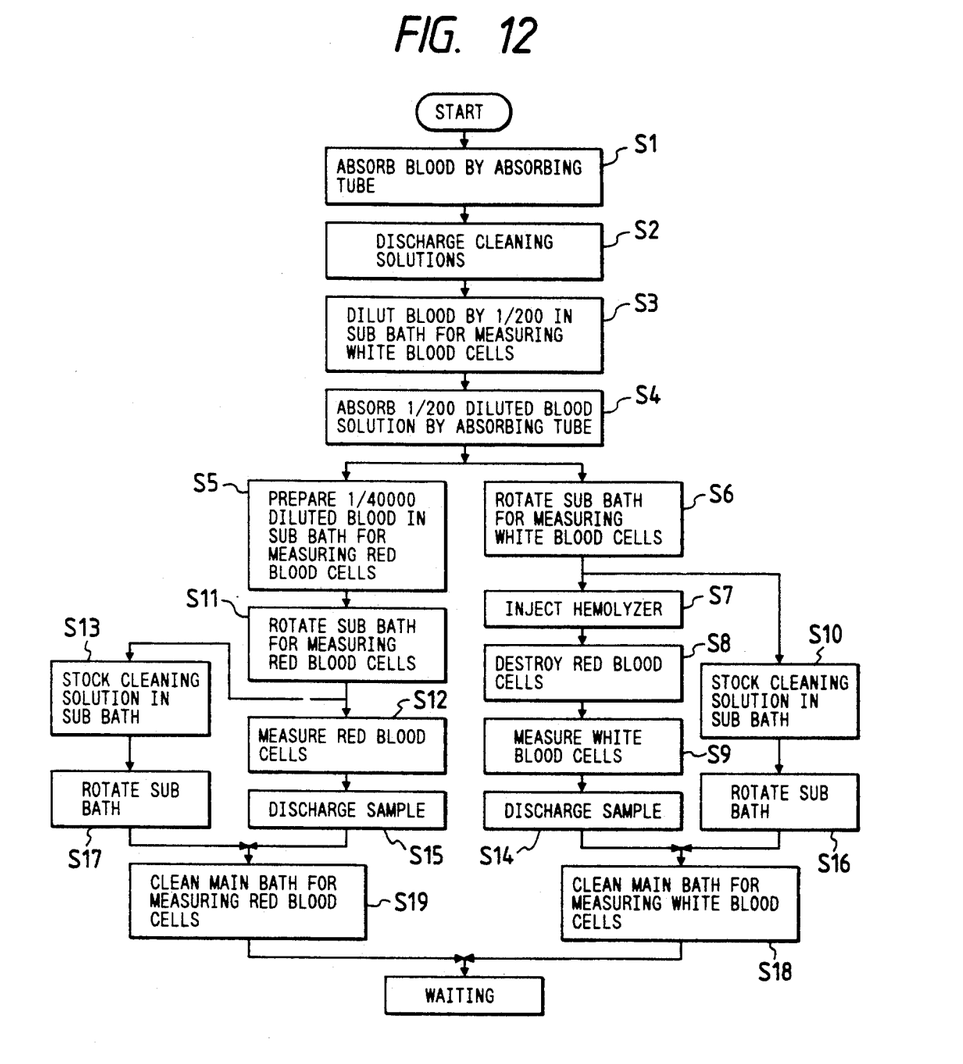
FIG. 12 is a flowchart showing the operation of the hematology analyzer of the invention.
Figure 13:
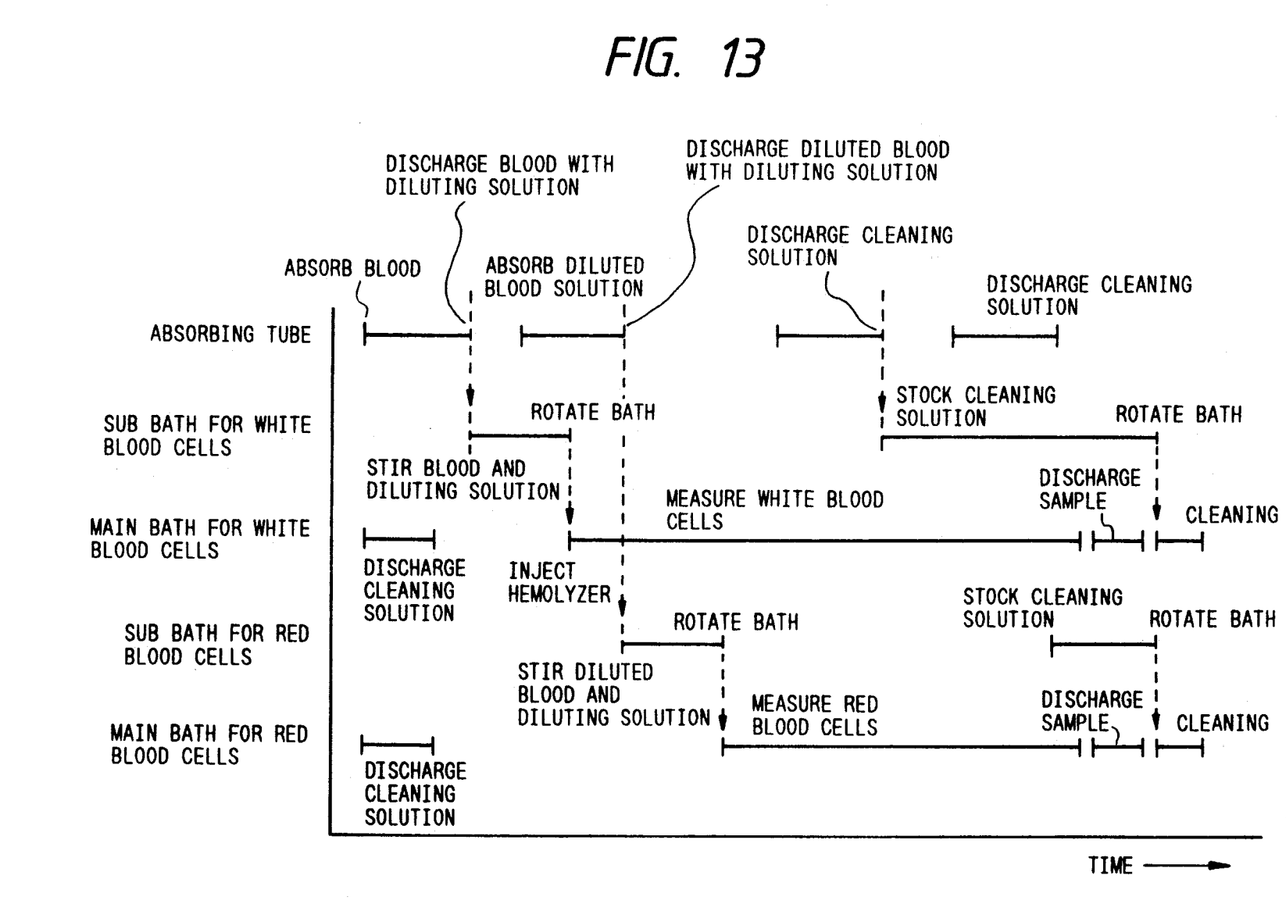
FIG. 13 is a diagram illustrative of a process of the hematology analyzer of the invention.

An operation of the thus constructed hematology analyzer will be described with reference to operation diagrams shown in FIGS. 1, 6 to 11 as well as to a flow diagram shown in FIG. 12 and a process diagram shown in FIG. 13.

As shown in FIG. 1, the blood 33 inside the sampling cup 32 is absorbed by, e.g., 50 μl using the sampling nozzle 16. Simultaneously therewith, cleaning solutions h1, h2 after the main baths 2, 3 have been cleaned are discharged.

Figure 6:
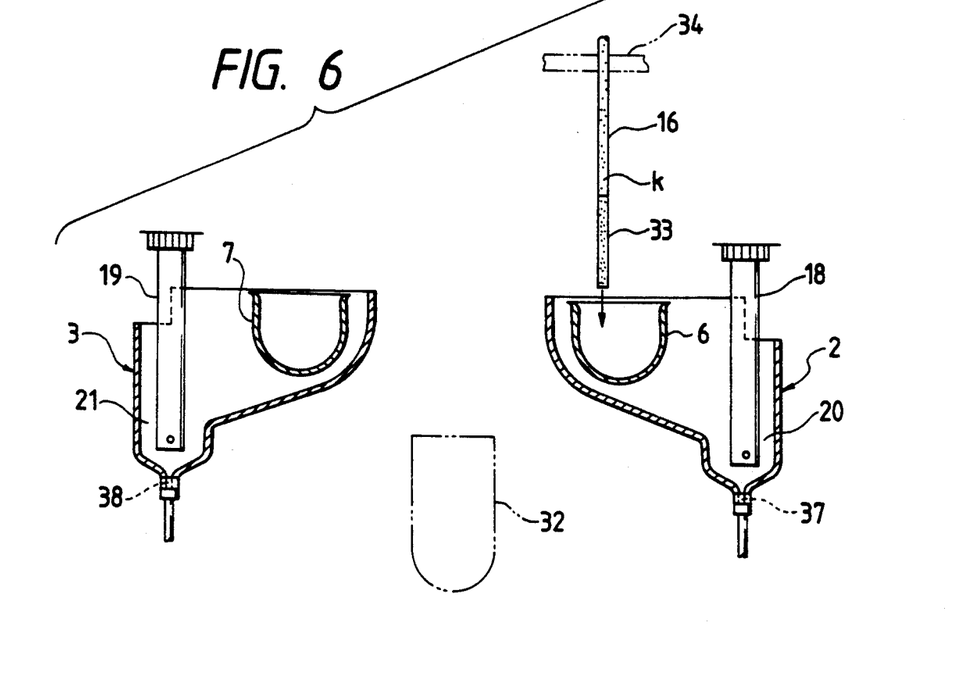
FIG. 6 is a diagram illustrative of an operation of the hematology analyzer of the invention.

Then, as shown in FIG. 6, the sampling nozzle 16 is transferred toward the sub bath 6 for measuring white blood cells, and 10 ml of diluting solution k is discharged into the sub bath 6 together with the blood 33 from the sampling nozzle 16. The blood and the diluting solution are stirred in the sub bath 6, with the blood being diluted by 1/200 (Steps S1 to S3).

Figure 7:
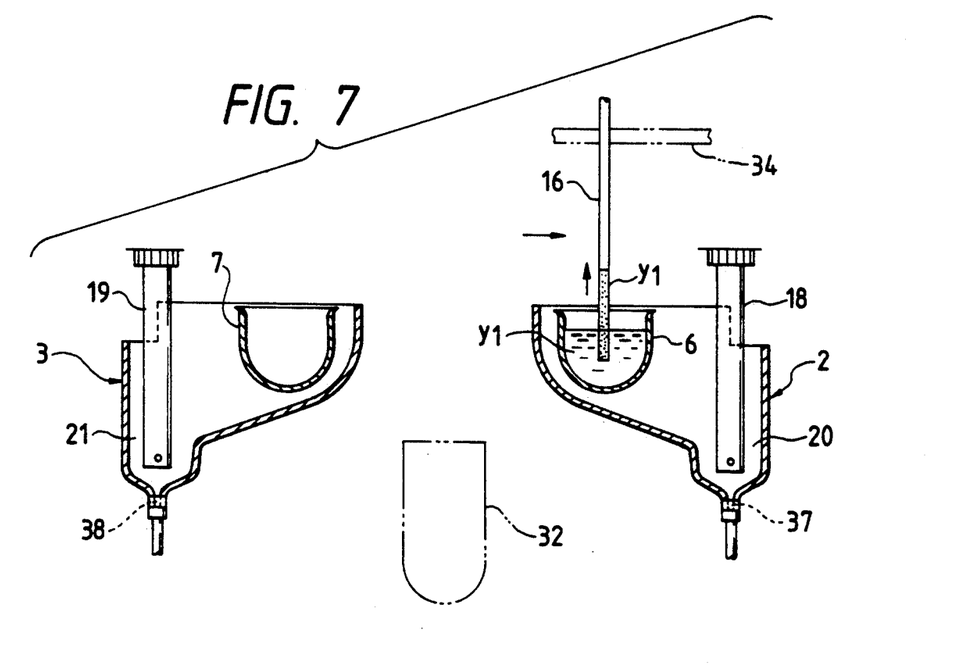
FIG. 7 is a diagram illustrative of the operation of the hematology analyzer of the invention.
Figure 8:
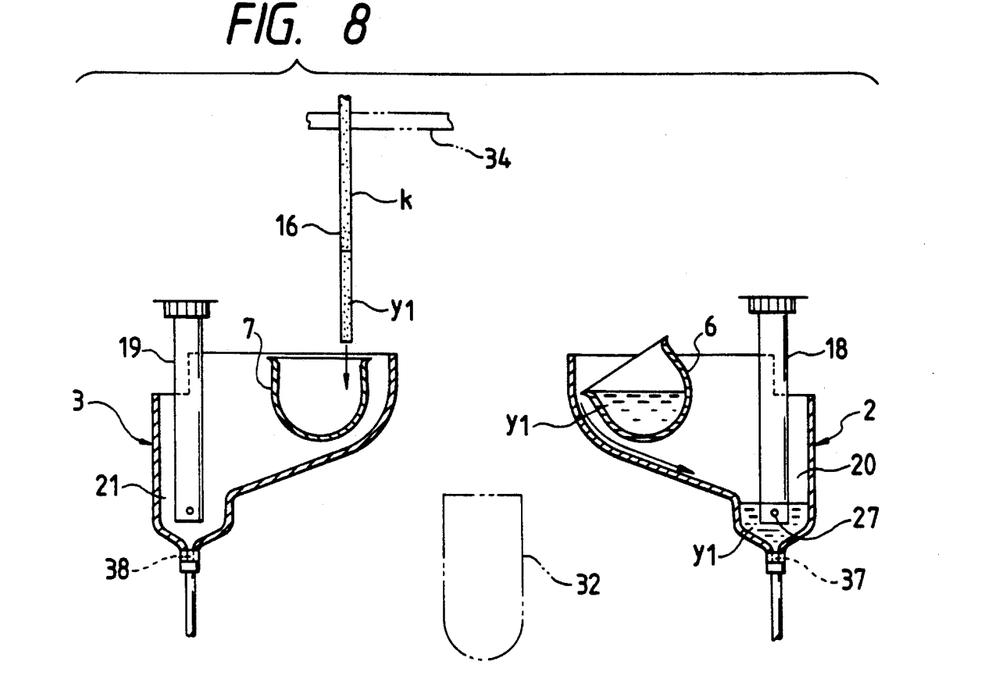
FIG. 8 is a diagram illustrative of the operation of the hematology analyzer of the invention.

Successively, as shown in FIG. 7, the 1/200 diluted blood solution y1 in the sub bath 6 is absorbed by 50 μl by the sampling nozzle 16 (Step S4). Thereafter, as shown in FIG. 8, the sampling nozzle 16 is transferred to the sub bath 7 for measuring red blood cells and from this sampling nozzle 16 the 1/200 diluted blood y1 and 10 ml of a diluting solution k are discharged into the sub bath 7. Accordingly, the 1/200 diluted blood solution and the diluting solution are stirred inside the sub bath 7 to be diluted further by 1/200 to prepare a 1/40000 diluted blood solution y2 (Step S5). At this point, the sub bath 6 for measuring white blood cells is rotated counterclockwise viewed from FIG. 8 by the driving of the motor 14, and the 1/200 diluted blood y1 in the sub bath 6 is poured into the measuring vessel 20 within the main bath 2. At this point, the hemolysing reagent is discharged from the injecting portion 23 and mixed with the diluted blood solution y1 while stirred by the swirling stream in the measuring vessel 20 to thereby destroy red blood cells in the diluted blood solution y1 (Steps S6 to S8).

Figure 9:
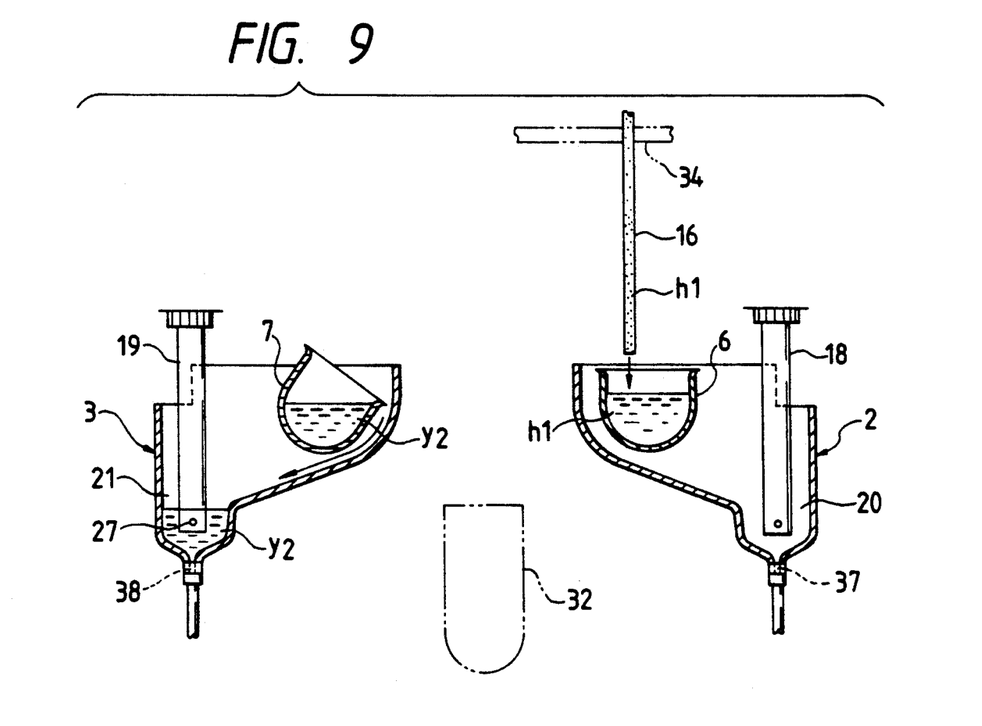
FIG. 9 is a diagram illustrative of the operation of the hematology analyzer of the invention.

Then, while the 1/200 diluted blood solution y1 in the measuring vessel 20 of the main bath 2 is being sucked up into the aperture tube 18, white blood cells passing through a hole 27 of the aperture tube 18 are sensed and the white blood cells are thereby measured (Step S9). As shown in FIG. 9, the cleaning solution h1 is poured by the sampling nozzle 16 and stocked in the sub bath 6 (Step S10). Also, the sub bath 7 for measuring red blood cells is rotated clockwise viewed from FIG. 9 by the driving of the motor 15 to allow the 1/40000 diluted blood solution y2 in the sub bath 7 to be poured into the measuring vessel 21 within the main bath 3 (Step S11).

Figure 10:
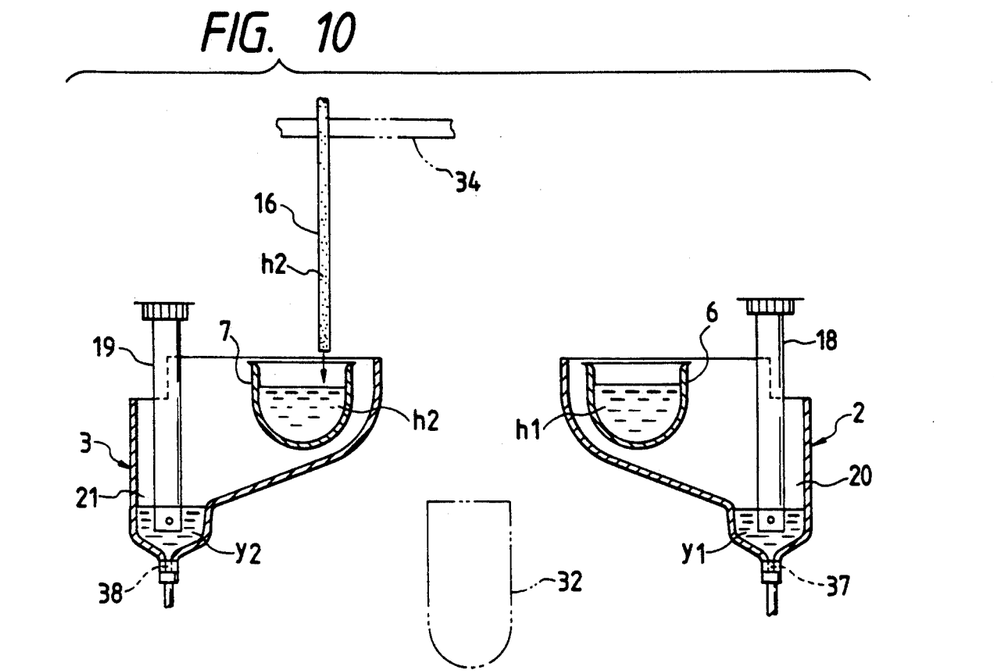
FIG. 10 is a diagram illustrative of the operation of the hematology analyzer of the invention.

Then, when the 1/40000 diluted blood solution y2 in the measuring vessel 21 of the main bath 3 is sucked up into the aperture tube 19, red blood cells passing through an aperture 27 of the aperture tube 19 are sensed and the red blood cells are thereby measured (Step S12). As shown in FIG. 10, the cleaning solution h2 is poured by the sampling nozzle 16 and stocked in the sub bath 7 (Step S13).

Figure 11:
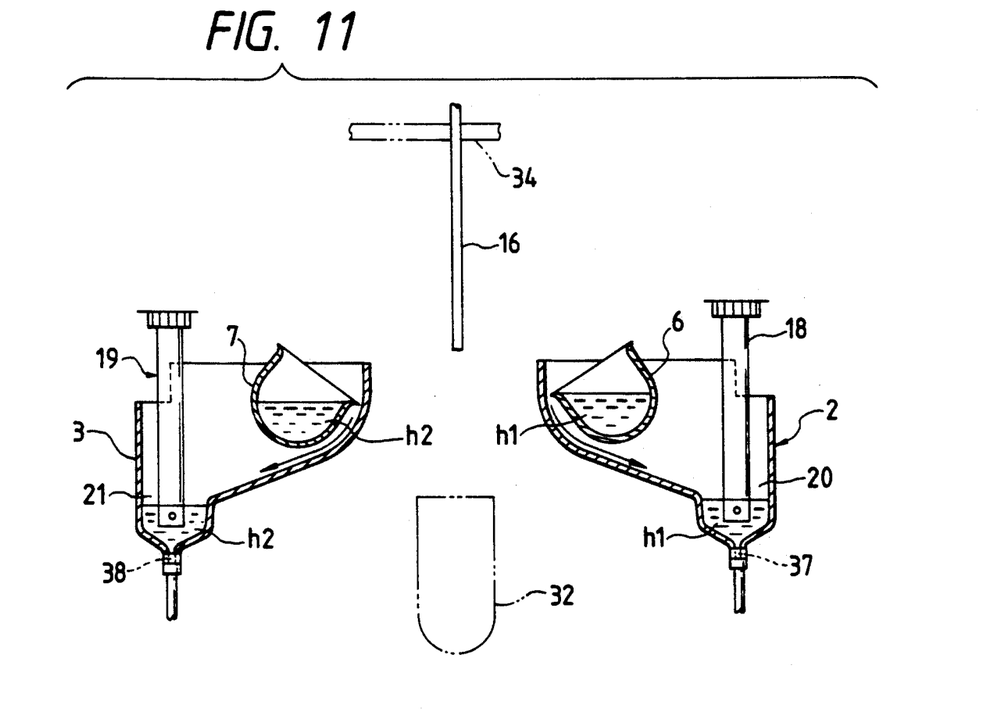
FIG. 11 is a diagram illustrative of the operation of the hematology analyzer of the invention.

Successively, the samples (y1, y2) in the main baths 2, 3 are totally discharged from discharging outlets 37, 38, respectively, and as shown in FIG. 11, the sub baths 6, 7 get rotated respectively to allow the cleaning solutions to be injected with force into the main baths 2, 3 to clean the main baths 2, 3 (Steps S14 to S19). Each of the main baths 2, 3 is then put in a standby position.

Thereafter, a next round of measurement is conducted based on a series of operations starting with Step S1. The feature of stocking the cleaning solutions h1, h2 in the sub baths 6, 7 while the blood cells are being measured so that the main baths 2, 3 can be cleaned upon completion of the measurement is beneficial in that the measurement time between the measurement start and the standby state can be shortened.

While the sub baths 6, 7 that are open on the top are rotatable to allow the solutions in the sub baths 6, 7 to be poured into the main baths 2, 3 in the above embodiment, it may be so designed that taps that can be opened and closed are provided at the bottoms of the sub baths 6, 7 to allow the solutions in the sub baths 6, 7 to be poured into the main baths 2, 3 through these tapes, respectively.

Each sub bath may not necessarily be disposed within each main bath separately, but may either be disposed outside the main bath at a position close thereto through a flow path or be integrated therewith. Further, each sub bath may not necessarily be rotatable, but may discharge the solution therein by the operation of a solenoid valve.

As described in the foregoing pages, the invention is so constructed that the auxiliary container (sub bath) is arranged inside or near the measuring container (main bath) and that the diluted blood solution prepared in the sub bath can directly be poured into the main bath. Therefore, the tubes and pneumatic source required by the conventional example to supply the diluted blood solution to the measuring cup can be dispensed with, thus allowing the apparatus to be made simple in structure. In addition, unlike the conventional example that supplies the diluted blood solution and the like through the tubes, the diluted blood solutions can be poured from a high position, and this not only ensures a high-speed and sure supply of solution, but also eliminates such conventional trouble as leak from and clogging of the tubes and defective supply of solution caused by such trouble.

Further, the provision of the sub bath that is open at the top so as to be rotatable inside the main bath allows the diluted blood solution in the sub bath to be poured into the main bath with so simple an operation of rotating the sub bath.

The shape of the sub bath can be designed arbitrarily as long as the blood can be diluted satisfactorily.

The shape of the main bath into which the diluted blood solution is poured from the sub bath can be designed arbitrarily as long as the diluted blood solution can be poured while forming a swirling stream. Therefore, the hemolysing reagent and the diluted blood solution which are poured can be stirred well. In addition the formation of a swirling stream within the main bath contributes to satisfactory cleaning of the main bath by the cleaning solution injected from the sub bath.

What is claimed is:

1. A diluting apparatus for use in a hematology analyzer that analyzes a sample of blood, the apparatus comprising:

a first measuring container;

a second measuring container;

first auxiliary container means for diluting blood collected by a sampling nozzle from the sample of blood with a diluting solution to form a first diluted blood solution flowing into said first measuring container; and second auxiliary container means for further diluting a portion of said first diluted blood solution with said diluting solution to form a second diluted blood solution flowing into said second measuring container, said first diluted blood solution being transmitted from said first auxiliary container means to said second auxiliary container means by said sampling nozzle;

wherein said first and second auxiliary container means are arranged to allow said first and second diluted blood solutions to pour into said first and second measuring container, respectively, and wherein said first and second auxiliary container means each have an upper opening portion, and said first and second auxiliary container means re rotatably coupled to said first and second measuring container to pour said first and second diluted blood solutions into said first and second measuring container respectively.

2. The apparatus as claimed in claim 1, wherein said first and second measuring containers have constricted flow paths for said first and second diluted blood solutions poured from said first and second auxiliary containers, respectively, to allow said first and second diluted blood solutions to be dashed into said first and second measuring containers, respectively, such that the diluted blood solutions are mixed.

3. The apparatus as claimed in claim 1, further comprising a first measurement means for detecting the number of white blood cells and a second measurement means for detecting the number of red blood cells.

4. The apparatus as claimed in claim 3, wherein said first measuring container has a liquid injecting portion for injecting a liquid toward said flow path of said first measuring container.

5. A diluting apparatus for use in forming diluted blood samples from a single whole blood sample, the apparatus comprising:
a sample distributor distributing dilution fluid and said blood sample;
first and second main chambers; and
first and second subchambers, respectively coupled to said first and second main chambers, each receiving at least said blood sample from said sample distributor, wherein said sample distributor pours a portion of said dilution fluid and said blood sample from a position above said first subchamber into said first subchamber, said first subchamber having a lower portion formed such that said portion of dilution fluid and the blood sample thus poured form a swirling stream, thereby mixing said portion of dilution fluid and the blood sample to form a first diluted blood sample;
wherein said first and second main chambers respectively include first and second measuring vessels for receiving diluted blood samples from said first and second subchambers, respectively and wherein said first and second subchambers are respectively coupled to said first and second main chambers such that said subchambers are rotated to respectively pour said first and second diluted blood samples into said first and second main chambers.

6. The diluting apparatus of claim 5, wherein said sample distributor transfers a portion of said first diluted blood sample formed in said first subchamber into said second subchamber, together with the remaining portion of said dilution fluid, said second subchamber having a lower portion formed such that said remaining portion of dilution fluid and the portion of said first blood sample form a swirling stream, thereby forming a second diluted blood sample.

7. The diluting apparatus of claim 6, wherein said first and second main chambers have bottom sloped surfaces forming fluid paths to said first and second measuring vessels, said paths being constricted such that said first and second diluted blood samples respectively form swirling streams in said first and second measuring vessels.

* * * * *